United States Patent [19]

Bosley, Jr.

[11] Patent Number: 5,514,176
[45] Date of Patent: May 7, 1996

[54] PULL APART COIL STENT

[75] Inventor: Rodney W. Bosley, Jr., Bloomington, Ind.

[73] Assignee: Vance Products Inc., Spencer, Ind.

[21] Appl. No.: 377,030

[22] Filed: Jan. 20, 1995

[51] Int. Cl.⁶ .................................................. A61F 2/06
[52] U.S. Cl. .............................. 623/1; 623/12; 606/156; 606/191
[58] Field of Search .................................... 623/1, 11, 12; 606/151, 153, 155, 156, 191, 197, 199

[56] References Cited

U.S. PATENT DOCUMENTS

| | | | |
|---|---|---|---|
| 3,562,820 | 2/1971 | Braun | 623/1 |
| 3,833,940 | 9/1974 | Hartenbach | 606/155 |
| 3,993,078 | 11/1976 | Bergentz et al. | 623/1 |
| 4,503,569 | 3/1985 | Dotter . | |
| 4,580,568 | 4/1986 | Gianturco . | |
| 4,601,713 | 7/1986 | Fuqua . | |
| 4,710,181 | 12/1987 | Fuqua . | |
| 4,738,666 | 4/1988 | Fuqua . | |
| 4,739,762 | 4/1988 | Palmaz . | |
| 4,820,298 | 4/1989 | Leveen et al. . | |
| 4,907,336 | 4/1990 | Gianturco . | |
| 5,098,374 | 3/1992 | Othel-Jacobsen et al. . | |
| 5,100,429 | 3/1992 | Sinofsky et al. | 606/195 |
| 5,222,971 | 6/1993 | Willard et al. | 606/198 |
| 5,242,451 | 9/1993 | Harada et al. | 623/12 |
| 5,246,445 | 9/1993 | Yachia et al. | 623/1 |

Primary Examiner—Paul B. Prebilic
Attorney, Agent, or Firm—Richard J. Godlewski

[57] ABSTRACT

A stent (10) adapted for placement in a body lumen (50) such as the urethra, ureters, common bile duct, vagina, cervix, fallopian tubes, sinus tract, rectum, bowel, esophagus or vascular system is configured as a coil (14) whose adjacent loops (12) can be pulled apart for removing the stent (10) from the body lumen (50). More particularly, the loops (12) abut one another but are not compressed, and adjacent coil loops are detachably secured to one another to yield a resilient configuration (17) of generally fixed dimension. The stent (10) is substantially imperforate between adjacent coil loops (12), so as to prevent tissue ingrowth or intrusion between them and obviate any interference with removal of the stent (10). Removal of the stent (10) from the body lumen (50) is achieved by detachment of adjacent coil loops (12) from one another. The adjacent coil loops (12) can be secured to one another directly during their curing, or by a separate layer of silicone adhesive (20). Indeed, a separate layer of silicone adhesive (20) can be applied to selectively adjust the parting strength of adjacent coil loops (12) which were self-adhered during curing. The loops (12) can be formed from a strand (30) of a physiologically acceptable metal wire, or from a continuous solid or tubular strand (18) of a medical grade silicone, fluorocarbon, rubber, latex, or vinyl or urethane polymer. The stent (10) is particularly advantageous over prior devices in reducing patient discomfort and the chance of tissue trauma or damage arising from removal of the stent (10) from the body lumen (50).

19 Claims, 3 Drawing Sheets

PULL APART COIL STENT

TECHNICAL FIELD

This invention relates generally to surgical devices, and more particularly to stents temporarily placed in various body cavities, vessels or ducts for expanding or maintaining an open lumen through them.

BACKGROUND OF THE INVENTION

Stents are a known class of surgical device for expanding or maintaining an open lumen or passageway through various body cavities, vessels or ducts. Locations in which stents are used include, but are not limited to, the urethra, the ureters, the common bile duct, the vagina, the cervix, the fallopian tubes, the sinus tract, the rectum, the bowel, the esophagus and the vascular tract.

While some stents are intended for long term use, there are numerous clinical applications in which stents are placed in the body only temporarily, for example, for temporary treatment of a medical problem, or to facilitate healing during a patient's recovery after a particular procedure. Laser ablation and cryoablation of the prostate are examples of such clinical applications. A short term (ten days to two weeks) indwelling stent ensures urethral and prostate patency after ablation.

It is highly desirable that any stents employed be removed from the body after such temporary uses. However, many stents possess open structures which permit the ingrowth or intrusion of tissue into them, or which permit the stents to embed themselves in the body tissues forming the cavities in which they are placed. Such ingrowth, intrusion or embedding makes it difficult to remove the stents without further trauma to the surgical site, causing discomfort to the patient and possibly delaying the patient's recovery from the particular procedure that has been performed.

For example, U.S. Pat. No. 4,503,569 (C. T. Dotter, Mar. 12, 1985) discloses a transluminally placed expandable graft prosthesis which includes a helically wound coil having a generally tubular shape. A version of a similar prosthesis is sold by Rabkin Corporation. The coil is made of a shape memory nitinol wire. The coil is placed in a blood vessel and is heated to its transition temperature, so as to expand and thereby keep the blood vessel open. However, the open configuration of the expanded coil permits prompt fibroblastic envelopment of the coil, firmly anchoring the coil within the blood vessel lumen. As a result, the coil cannot be removed from the body without surgical cutting.

Another type of helical vascular stent is disclosed in U.S. Pat. No. 4,820,298 (E. G. Leveen et al., Apr. 11, 1989) and includes a helix composed of a medical grade thermoplastic with strands of material extending between the spaced apart coils of the helix. The strands promote cellular ingrowth between the coils, so that removal of the stent similarly requires surgical cutting.

Yet another type of device is shown in U.S. Pat. No. 5,098,374 (E. Othel-Jacobsen et al., Mar. 24, 1992). A version of a similar stent is sold under the registered trademark "PROSTAKATH" by Endovision Pry. Ltd., Victoria, Australia. The device is a partial catheter formed of a wire coil having two pluralities of coil turns separated by a straight or rod-like segment. The catheter is asserted to be removable from the vessel or duct in which it is positioned by manipulation with forceps. However, because the spaces between the coil turns of the catheter permit tissue ingrowth and crystalline formation on and between the coil turns, the catheter becomes enmeshed with the vessel wall and is difficult to remove without trauma to the vessel wall, and bleeding and discomfort to the patient.

U.S. Pat. No. 4,580,568 (C. Gianturco, Apr. 8, 1986), No. 4,739,762 (J. C. Palmaz, Apr. 26, 1988) and No. 4,907,336 (C. Gianturco, Mar. 13, 1990) all disclose expanding wire stents of cylindrical shape, which are compressed by a removable sheath to facilitate their introduction into the lumen of a blood vessel or other body portion. (The first of these is sold under the name "Z-stent," a tradename of Cook Incorporated.) The sheath is withdrawn after the stent is positioned, and the stent self-expands ('568) or is expanded by a balloon catheter ('762 and '336) so as to keep the lumen open. Unfortunately, it has been found during the use of self-expanding stents of this and other types that the stents may continue to expand beyond the normal diameter of the passageway in which they are positioned. Thus, in some cases the stents become deeply embedded in the walls of the passageway. While this problem has been partially overcome by the use of flexible but inelastic rings to limit expansion of the stents, tissue ingrowth during their use remains a problem.

Tissue ingrowth can be obviated by the use of a variable diameter catheter, such as shown in U.S. Pat. No. 4,601,713 (C. R. Fuqua, Jul. 22, 1986), No. 4,710,181 (C. R. Fuqua, Dec. 1, 1987) and No. 4,738,666 (C. R. Fuqua, Apr. 19, 1988). Catheters of this type include a longitudinally extending folded wall, and during introduction into a body orifice the wall is held in place by a removable styler or sheath, whose removal allows expansion of the diameter of the catheter. Unfortunately, precisely because that wall is foldable, such catheters do not provide structural support for maintaining an open lumen in the body orifice. Moreover, such catheters lack any means to reduce the catheter diameter during removal of the catheter from the body orifice.

SUMMARY OF THE INVENTION

The foregoing problems are solved and a technical advance is achieved in an illustrative stent useful for establishing or maintaining a lumen through any of a wide variety of body cavities, vessels and ducts. More particularly, it has been discovered that a plurality of relatively flexible, uncompressed coil loops can be abutted and detachably secured to one another so as to yield a resilient configuration whose dimensions are generally fixed, that is, sufficiently fixed to allow the configuration to function as a stent; and further discovered that the stent so formed can readily be removed from the lumen by detachment of the loops from one another, provided that when the abutted loops are secured to one another, the stent so formed is substantially imperforate between adjacent coil loops.

With regard to the flexibility of the coil loops, "relatively" means that the loops are sufficiently flexible when detached from one another to permit removal of the loops from the body lumen in which the stent is positioned, for example, by achieving an elongated shape of reduced outside diameter, narrower than the diameter of the body lumen. Existing metallic stents are far too stiff to allow their removal from the body lumen in such a manner. Moreover, since the coil loops of the stent of the present invention are uncompressed, there is no force urging the stent to expand beyond its initial diameter, obviating any penetration of the coil loops into the wall defining the body lumen.

With regard to the imperforate nature of the stent, "substantially" means merely that undesirable tissue ingrowth or intrusion between adjacent coil loops of the stent is, in fact, prevented or minimized. As will be understood by those skilled in this art, the word is used qualitatively, and is not intended to indicate a specific quantitative limit on such intrusion.

In a first aspect, then, the present invention is directed to a pull apart coil stent placeable in a body lumen such as the urethra, the ureters, the common bile duct, the vagina, the cervix, the fallopian tubes, the sinus tract, the rectum, the bowel, the esophagus or the vascular tract, and which comprises a plurality of uncompressed abutted loops arranged as an open-ended coil, the adjacent coil loops being detachably secured to one another to yield a resilient configuration of generally fixed dimension, wherein the stent is substantially imperforate between adjacent coil loops. The coil loops are preferably formed from a continuous strand of a physiologically acceptable metal wire; from a strand or tube of a medical grade silicone, fluorocarbon, rubber, latex, vinyl or urethane polymer, or the like; or from such a tube containing in it a physiologically acceptable metal wire. The coil loops can be secured directly to one another during their curing (if made from silicone or the like), or by a separate layer of a medical grade adhesive. Preferably, the medical grade adhesive is applied to loops which are already self-adhered, thereby allowing selective adjustment of the parting strength of the adjacent coil loops.

In a second aspect, the present invention is directed to a pull apart coil stent which includes a means for detachably securing adjacent coil loops to one another, and in which it is this securing means that also renders the stent substantially imperforate between adjacent coil loops. The securing means of the present invention is clearly distinct from the sheaths employed to introduce many of the existing stents mentioned as background above, because such sheaths generally (a) are not employed with stents which can be readily collapsed for removal from the body lumen; (b) do not serve to hold uncompressed coil loops in abutment; (c) do not remain in place while the coil loops hold the lumen open; and (d) are not collapsible and removable from the lumen once the underlying stent has been removed. The securing means can be or can include the separate layer of medical grade adhesive. Preferably, however, the securing means is or includes the partable layer formed from and between adjacent coil loops during their curing.

In a final aspect, the present invention is directed to a pull apart coil stent comprising or consisting of certain parts of the preferred embodiment set forth below.

BRIEF DESCRIPTION OF THE DRAWING

A better understanding of the present invention will now be had upon reference to the following detailed description, when read in conjunction with the accompanying drawing, wherein like reference characters refer to like parts throughout the several views, and in which.

DETAILED DESCRIPTION

Figure 1:
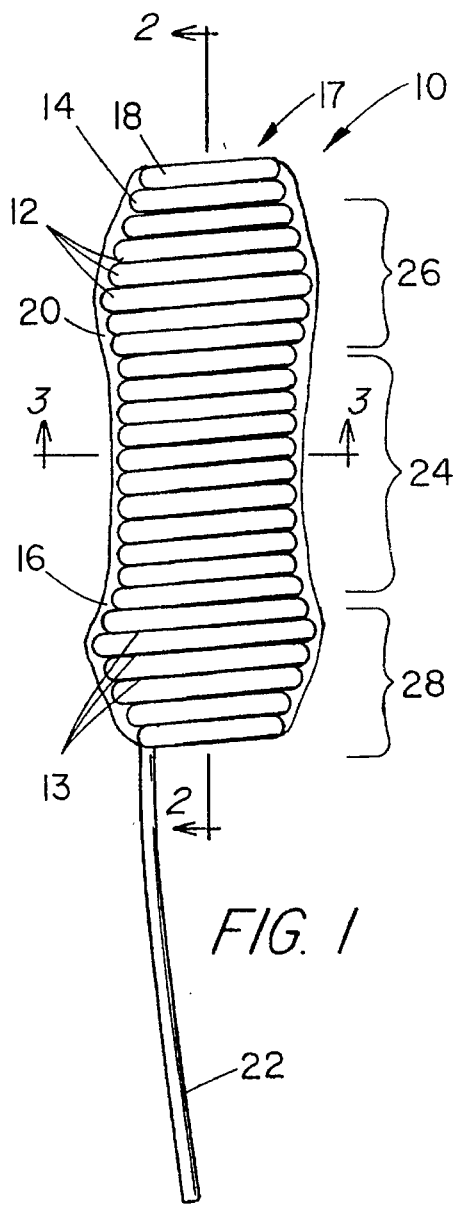
FIG. 1 is a side view of the preferred embodiment of the present invention.
Figure 2:
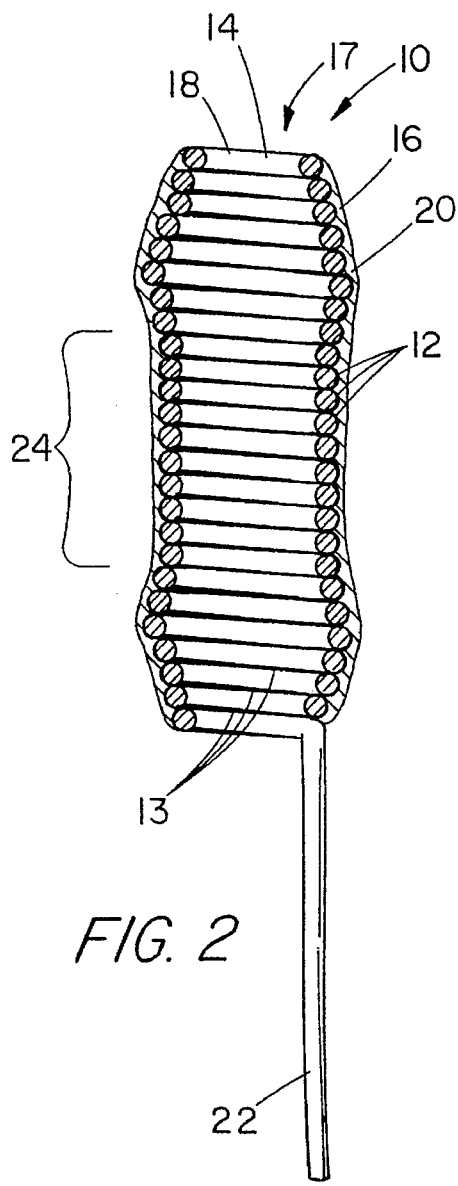
FIG. 2 is a cross-sectional view taken along line 2—2 of FIG. 1.
Figure 3:
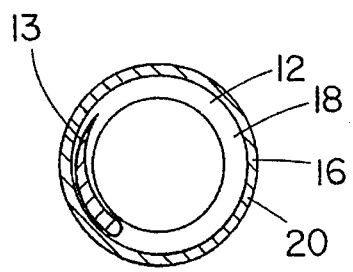
FIG. 3 is a cross-sectional view taken along line 3—3 of FIG. 1.

With reference first to FIGS. 1 through 3, a first preferred embodiment of the pull apart coil stent 10 of the present invention is thereshown and comprises a plurality of uncompressed abutted loops 12 arranged as an open-ended coil 14. The adjacent coil loops 12 are detachably secured to one another to yield a resilient configuration 17 of generally fixed dimension, in which the stent 10 is substantially imperforate between the adjacent coil loops 12. More particularly, the adjacent coil loops 12 are detachably secured to one another by a means 16 which also preferably simultaneously renders the stent 10 substantially imperforate between adjacent loops 12.

The securing means 16 comprises at least one of, and preferably both of, (a) a medical grade liquid silicone adhesive 20 on the adjacent coil loops 12; and (b) a partable layer 13 between the adjacent coil loops 12, continuously formed with the loops 12. Although shown in FIG. 1 as being generally positioned on the outer surface of the coil 14, the silicone adhesive 20 can be positioned on the inner surface of the coil 14, or can be positioned between the individual loops 12 of the coil 14, replacing the partable layer 13.

The securing means 16 can alternatively comprise only the medical grade silicone adhesive 20 securing otherwise unattached adjacent loops 12 of the coil 14 to one another. Similarly, the securing means 16 can alternatively comprise only the partable layer 13 between adjacent coil loops 12.

The coil loops 12 can be formed from a continuous strand of any medical grade or physiologically acceptable material. For example, the loops 12 can be formed from a continuous solid or tubular strand 18 of a curable medical grade silicone, fluorocarbon, rubber, latex, or vinyl or urethane polymer, or the like. Preferably, the strand 18 is composed of Dow Corning medical grade silicone.

The stent 10 preferably includes a graspable tag end 22 continuously and unitarily formed with the strand 18. The strength with which the securing means 16 holds the coil loops 12 together is selected so that when the stent 10 is positioned within a body lumen, grasping and pulling on the tag end 22 (in a fashion more fully explained below) separates adjacent coil loops 12 from one another, allowing removal of the stent 10 from the lumen.

The stent 10 is preferably shaped so that, while its configuration 17 is generally cylindrical in shape, the configuration 17 includes a medial portion 24 having a generally uniform diameter, and at least one end portion (either or both of an end portion 26 opposite the tag end 22, and an end portion 28 proximal to the tag end 22) having an outside diameter greater than the outside diameter of the medial portion 24. The larger diameter on the end portions 26 or 28 facilitates introduction of the stent 10 into the desired body lumen, and prevents migration of the stent 10 in the body lumen in which it is placed.

Figure 4:
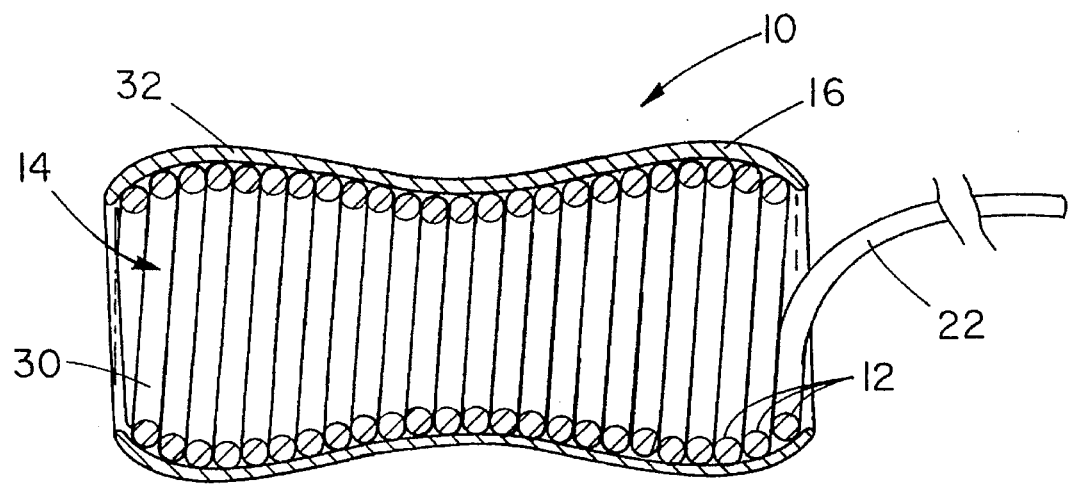
FIG. 4 is a cross-sectional view of another preferred embodiment of the present invention, similar to the view of FIG. 2.

Another preferred embodiment of the stent 10 of the present invention is shown in FIG. 4, in which the loops 12 of the coil 14 are formed from a continuous strand 30 of a physiologically acceptable metal wire. The strand 30 can be composed of silver, tantalum, stainless steel, gold or titanium. Preferably, however, the strand 30 is composed of nitinol wire, whose superelasticity facilitates both manufacture of the stent 10 and its removal from the patient's body. In this embodiment, the securing means 16 comprises a plastic shrink-wrap tube 32 positioned about the coil 14. The use of a medical grade silicone adhesive as previously described can be used for tube 32. Silicone adhesive would adhere the loops together and pull apart with the loops during removal. Other types of plastic or other tube are also expected to be useful for this purpose, so long as the tube 32 can be collapsed for removal from the body lumen, once the coil loops 12 are detached from one another (by pulling them from the shrink-wrap tube 32) and the coil 14 removed from the body lumen.

Figure 5:
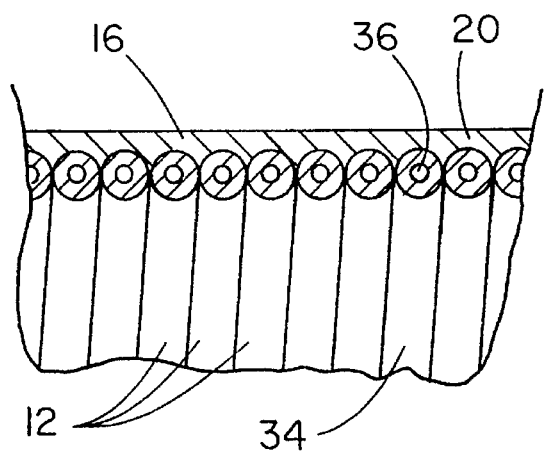
FIG. 5 is a cross-sectional view of a portion of another preferred embodiment of the present invention.

With reference next to FIG. 5, another preferred embodiment of the present invention is shown in which the coil loops 12 are formed from a tube 34 having a lumen 36 formed longitudinally in it. The tube 34 can be composed of any of the materials used for the continuous strand 18 of the embodiment disclosed in FIGS. 1 through 3. A tube of silicone is used to also vary the radial compression of the coil stent as physiologically needed to meet different anatomical sites.

Figure 6:
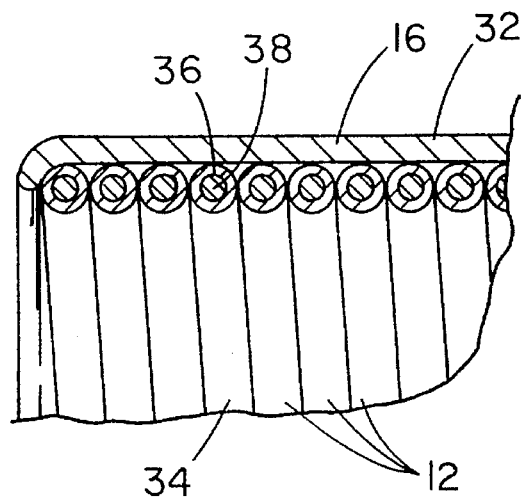
FIG. 6 is a cross-sectional view of a portion of another preferred embodiment of the present invention.

A related embodiment of the present invention is shown in FIG. 6, in which a strand 38 of a different material is contained in the lumen 36 of the tube 34 making up the coil loops 12. The strand 38 can be composed of any suitable plastic or other material which is stiffer than the material of the tube 34. Preferably, however, the strand 38 is composed of a physiologically acceptable metal wire, such as any of the materials used for the strand 30 in the embodiment shown in FIG. 4, most preferably nitinol wire.

The particular dimensions of the coil loops 12 and resilient configuration 17, as well as the tensile or parting strength of the silicone adhesive 20 and/or the partable layer 13 (or of any other securing means 16) must be selected in view of the specific body lumen in which the stent 10 is intended to be positioned. The selection of those dimensions and characteristics will fall well within the abilities of anyone even rudimentarily skilled in this area, in view of the functional requirements described herein, and for brevity will generally not be described further.

Solely for illustrative purposes, however, it should be noted that the stent 10 shown in FIGS. 1 through 3 is drawn to proportion (other than the length of the tag end 22) and is intended for use in the urethra, more particularly for retention within the prostate gland during ablative surgery. The silicone strand 18 possesses a circular cross-section and has a diameter of about 4 French. For use within the prostate gland, it has been found that a solid strand 18 possesses an unfavorably high parting strength, so that a tubular cured strand 18 (comparable to the tube 34 of FIG. 5) is decidedly preferred. The opposite and proximal end portions 26 and 28 of the stent 10 have outer diameters of about 22 and 20 French, respectively, while the medial portion 24 has an outer diameter of about 18 French. The end portions 26 and 28 each extend about 4 mm longitudinally, while the overall length of the coil 14 (that is, of the medial portion 24 and the end portions 26 and 28) is about 3 cm. The tag end 22 of the stent 10 is about 12 cm long prior to introduction into the body lumen. The interior diameter of the stent 10 at the medial portion 24 is about 10 French. Lastly, the layer of medical grade adhesive 20 is about 0.006 inches thick, applied as three 0.002 inch layers.

Again, these dimensions are recited to illustrate a stent 10 intended for positioning in the urethra during and after prostate ablation, and the dimensions of the stent will have to be selected by the practitioner for the particular body lumen in which the stent will be placed. The end portions 26 and 28 of the stent 10, for example, serve to position and retain the stent 10 with respect to the prostate gland, and such portions may or may not be useful in particular applications.

Construction of the stent 10 of the present invention is straightforward. The solid or tubular strand 18 is first extruded from a curable medical grade silicone or the like. The strand 18 is then wrapped about a cylindrical mandrel or other form (not shown) so as to form the plurality of loops 12 in abutment with one another, in the shape of the coil 14. The strand 18 is cured in any conventional fashion, such as by heating, ultrasonic welding, light activated surface modification, or the like, so as to form the partable layers 13 between adjacent coil loops 12. The partable layers 13 can instead be formed by the sputtering, chemical grafting, ion implantation or ion deposition of an additional coating, or by plasma polymerization of the surface of the strand 18.

The liquid silicone adhesive 20 is then applied to the coil loops 12, such as by pouring over, painting, spraying or dipping. The stent 10 is then removed from the mandrel or form, ready for introduction into the desired body lumen. Of course, as mentioned above, the silicone adhesive 20 may instead be applied beneath or between the coil loops 12. If so, the silicone adhesive 20 is applied to the mandrel or to the loops 12 themselves before or during wrapping of the loops 12 about the mandrel, as appropriate. Most preferably, as indicated above, the coil loops 12 are self-secured to one another, and the silicone adhesive 20 used merely to adjust the parting strength of the loops 12.

Introduction of the stent 10 into a desired body lumen and removal of the stent 10 from the body lumen are also straightforward. In describing the introduction and removal procedures, a familiarity with the various conventional procedures for the use of the several prior stents discussed as background above will be presumed.

Figure 7:
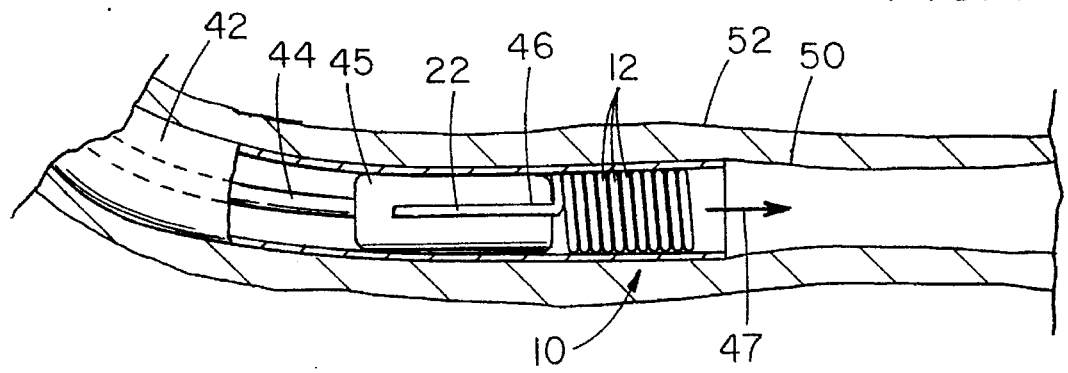
FIGS. 7 through 9 are schematic views of the use of the preferred embodiment of the present invention.

As shown in FIG. 7, the stent 10 of the present invention is introduced into a desired body lumen 50 by means of a catheter 42 passed through or beneath the skin 52 of the patient. The stent 10 is contained within the catheter 42 and lies against a piston or pushing element 45. The piston 45 is connected to a push rod 44 slidably contained in but extending outwardly of the catheter 42 and the patient's body, and includes a recess 46 for receiving the tag end 22 of the stent 10, so that the tag end 22 does not interfere with the smooth sliding of the piston 45 and stent 10 through the catheter 42.

Figure 8:
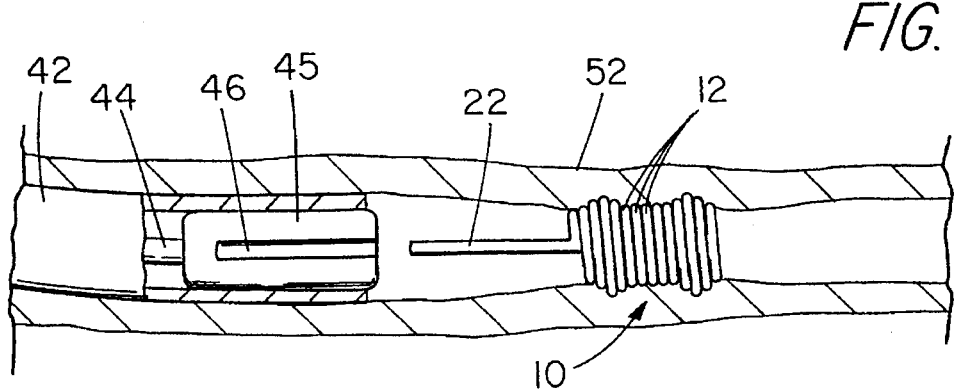

Once the catheter 42 is properly positioned in the body lumen 50, the push rod 44 is manipulated to move the piston 45 and the stent 10 in the direction of arrow 47, until the stent 10 achieves the position shown in FIG. 8, free from the catheter 42. The resiliency of the stent 10 minimizes the patient's discomfort during introduction and may facilitate proper positioning of the stent 10 in the body lumen 50. The catheter 42 and piston 45 are then slightly withdrawn from the stent 10, the piston 45 retracted into the catheter 42, and the catheter 42 (containing the push rod 44 and the piston 45) withdrawn from the body lumen 50.

The stent 10 keeps the lumen open like prior stents, but avoids the problems associated with them. Because the coil loops 12 of the stent 10 are uncompressed, unlike several prior stents there is no shape memory or restorative force which would cause the loops 12 to embed or implant in the wall defining the body lumen 50. Further, because the stent 10 is substantially imperforate between the coil loops 12, unlike several prior stents there is generally no tissue ingrowth or intrusion between the coil loops 12.

Figure 9:
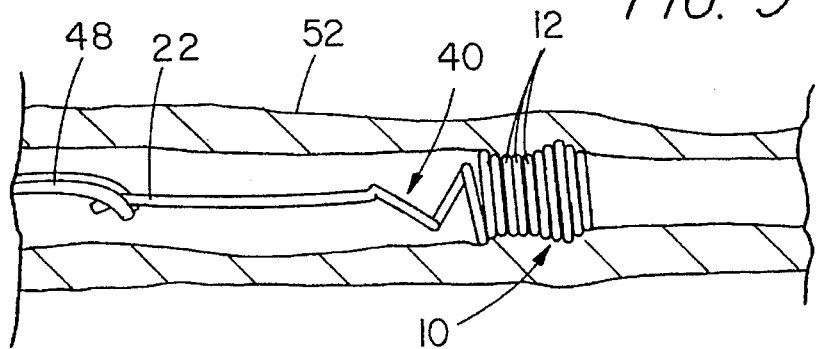

Even if a minor amount of ingrowth or intrusion is encountered, the structure of the stent 10 permits its removal from such ingrowth or intrusion without significant trauma to the wall of the body lumen 50. Such removal is shown schematically in FIG. 9, in which a grasping device exemplified by forceps 48 is used to engage and remove the stent 10 from the body lumen 50. More particularly, the forceps are used to grasp the tag end 22 of the stent 10 and separate adjacent coil loops 12 from one another by pulling the tag end 22 in a direction out of the lumen 50 and out of the patient's body. This pulling action forms the separated loops 12 into a pulled shape 40 of a diameter less than the diameter of the remainder of the stent 10, and less than the diameter of the body lumen 50. This allows the separated loops 12 to be freely withdrawn from the lumen 50. Optimally, the pulling action of the forceps 48 causes the loops 12 to separate completely from one another, so that the pulled shape 40 is fully uncoiled, and is essentially straight and flexible. Thus, even if some minor amount of tissue ingrowth or intrusion between the coil loops 12 has occurred, separation of the loops 12 during removal allows them to be individually detached with minimal trauma to the lumen wall, and thus minimal discomfort to the patient and minimal interference with the recovery of the patient.

INDUSTRIAL APPLICABILITY

The present invention is useful in the performance of surgical procedures, and therefore finds applicability in human and veterinary medicine.

It is to be understood, however, that the above-described stent or the like is merely an illustrative embodiment of the principles of this invention, and that other stents or the like and methods for using them may be devised by those skilled in the art, without departing from the spirit and scope of the invention. It is also to be understood that the invention is directed to embodiments both comprising and consisting of the disclosed parts.

What is claimed is:

1. A pull apart coil stent (10) placeable in a body lumen (50) comprising a plurality of uncompressed abutted loops (12) arranged as an open-ended coil (14), and a medical grade adhesive detachably securing adjacent coil loops to one another to yield a resilient configuration (17) of generally fixed dimension, wherein the stent (10) is substantially imperforate between adjacent coil loops.

2. The stent according to claim 1, wherein the loops (12) are formed from a continuous strand (30) of a physiologically acceptable metal wire.

3. The stent according to claim 1, wherein the loops (12) are formed from a continuous strand (18) of a medical grade silicone, fluorocarbon, rubber, latex, vinyl polymer or urethane polymer.

4. The stent according to claim 3, wherein the loops (12) are formed from a tube (34) having a lumen (36) therein.

5. The stent according to claim 4, further comprising a strand (38) of a physiologically acceptable metal wire contained in the tube lumen (36).

6. The stent according to claim 1, further comprising a tag end (22) formed continuously with the plurality of loops (12).

7. The stent according to claim 1, wherein adjacent coil loops (12) are secured to one another by a partable layer (13) formed from and between the adjacent coil loops (12).

8. The stent according to claim 1, wherein said medical grade adhesive comprises a medical grade silicone adhesive (20).

9. The stent according to claim 1, wherein the coil (14) includes a medial portion (24) and at least one end portion (26 or 28) having an outside diameter greater than the outside diameter of the medial portion (24) of the coil (14).

10. A pull apart coil stent (10) placeable in a body lumen (50) comprising a plurality of uncompressed abutted loops (12) arranged as an open-ended coil (14), and medical grade adhesive means (16) for detachably securing adjacent coil loops to one another to yield a resilient configuration (17) of generally fixed dimension, the medical grade adhesive means (16) also rendering the stent (10) substantially imperforate between adjacent coil loops.

11. The stent according to claim 10, wherein the loops (12) are formed from a continuous strand (30) of a physiologically acceptable metal wire.

12. The stent according to claim 10, wherein the loops (12) are formed from a continuous strand (18) of a medical grade silicone, fluorocarbon, rubber, latex, vinyl polymer or urethane polymer.

13. The stent according to claim 12, wherein the loops (12) are formed from a tube (34) having a lumen (36) therein.

14. The stent according to claim 13, further comprising a strand (38) of a physiologically acceptable metal wire contained in the tube lumen (36).

15. The stent according to claim 10, further comprising a tag end (22) formed continuously with the plurality of loops (12).

16. The stent according to claim 10, wherein the securing means (16) comprises a partable layer (13) formed from and between adjacent coil loops (12).

17. The stent according to claim 10, wherein the medical grade adhesive means (16) comprises a medical grade silicone adhesive (20) securing adjacent loops of the coil (14) to one another.

18. The stent according to claim 10, wherein the coil (14) includes a medial portion (24) and at least one end portion (26 or 28) having an outside diameter greater than the outside diameter of the medial portion (24) of the coil (14).

19. A pull apart coil stent (10) placeable in a body lumen (50) comprising:

a plurality of uncompressed abutted loops (12) arranged as an open-ended coil (14), the loops (12) being formed from a continuous strand (18) of medical grade silicone, and adjacent coil loops (12) being detachably secured to one another by a partable layer (13) formed from and between the adjacent coil loops (12) and by a medical grade silicone adhesive (20) so as to yield a resilient cylindrical configuration (17) of generally fixed dimension; and a tag end (22) formed continuously with the plurality of loops (12);

wherein the partable layer (13) and the silicone adhesive (20) render the stent (10) substantially imperforate between adjacent coil loops, such that when adjacent loops are detached from one another, the stent (10) can be pulled to yield an elongated shape (40) of reduced outside diameter, permitting withdrawal of the stent (10) from the lumen (50) in which it was positioned.

* * * * *